United States Patent
Xu et al.

(10) Patent No.: US 11,138,726 B2
(45) Date of Patent: Oct. 5, 2021

(54) METHOD, CLIENT, SERVER AND SYSTEM FOR DETECTING TONGUE IMAGE, AND TONGUE IMAGER

(71) Applicant: BOE TECHNOLOGY GROUP CO., LTD., Beijing (CN)

(72) Inventors: Zhihong Xu, Beijing (CN); Hongwen Zhu, Beijing (CN)

(73) Assignee: BOE Technology Group, Co., Ltd., Beijing (CN)

( * ) Notice: Subject to any disclaimer, the term of this patent is extended or adjusted under 35 U.S.C. 154(b) by 214 days.

(21) Appl. No.: 16/407,997

(22) Filed: May 9, 2019

(65) Prior Publication Data
US 2020/0160512 A1    May 21, 2020

(30) Foreign Application Priority Data
Nov. 16, 2018    (CN) .......................... 201811372083.1

(51) Int. Cl.
*G06T 7/00* (2017.01)
*G16H 30/20* (2018.01)
*G06N 3/08* (2006.01)

(52) U.S. Cl.
CPC ............. *G06T 7/0012* (2013.01); *G06N 3/08* (2013.01); *G16H 30/20* (2018.01); *G06T 2207/30004* (2013.01)

(58) Field of Classification Search
CPC ......... G06T 7/0012; G06T 2207/20081; G06T 2207/30004; G16H 30/20; G16H 50/20; G06K 2209/05; G06N 3/08

USPC ........................................................ 382/128
See application file for complete search history.

(56) References Cited

U.S. PATENT DOCUMENTS

2008/0139966 A1*    6/2008    Zhang ................ A61B 5/7267
                                                 600/590

OTHER PUBLICATIONS

Computer English Translation of Chinese Patent No. CN108461142A (Year: 2018).*
Computer English Translation of Chinese Patent No. CN104298983B (Year: 2018).*

* cited by examiner

*Primary Examiner* — Daniel G Mariam
(74) *Attorney, Agent, or Firm* — The Webb Law Firm (57) ABSTRACT

The present disclosure relates to a method, a client, a server and a system for detecting a tongue image, and a tongue imager. The method for detecting the tongue image, which is applied to the client for detecting the tongue image, comprises: acquiring the tongue image, recognizing the tongue image by using an image analysis model, and generating and displaying a first label information; determining, after acquiring a correction information for the first label information, whether to adopt the correction information in accordance with an accuracy corresponding to the correction information, and generating a second label information; and analyzing the tongue image and the second label information by using an assistant diagnosis model, and generating an assistant diagnosis result.

12 Claims, 4 Drawing Sheets

--- acquiring a tongue image, recognizing the tongue image by using an image analysis model, and generating and displaying a first label information  ⟶ S110 determining, after acquiring a correction information for the first label information, whether to adopt the correction information in accordance with an accuracy corresponding to the correction information, and generating a second label information  ⟶ S120 analyzing the tongue image and the second label information by using an assistant diagnosis model, and generating an assistant diagnosis result  ⟶ S130

METHOD, CLIENT, SERVER AND SYSTEM FOR DETECTING TONGUE IMAGE, AND TONGUE IMAGER

CROSS REFERENCE TO RELATED APPLICATIONS

This application claims priority to Chinese Patent Application No. 201811372083.1, as filed on Nov. 16, 2018, the disclosure of which is incorporated herein in its entirety by reference.

TECHNICAL FIELD

The present disclosure relates to the technical field of the medical appliance, and in particular, to a method, a client, a server and a system for detecting a tongue image, and a tongue imager.

BACKGROUND

Tongue diagnosis is one of basic clinical diagnosis methods of the Traditional Chinese Medicine (TCM). By the tongue diagnosis, doctors may analyze Blood-Qi rise and fall of human body viscera, viscera where diseases reside, and changes of the diseases. It has a significant reference meaning for prescription medication and disease prognosis determination of the TCM.

To implement quantification and standardization of the TCM diagnosis, a tongue imager has been developed. Pursuant to tongue diagnosis principles of the TCM, the tongue imager is developed by using advanced digital cameras and computer techniques, which is an instrument that extracts and processes a feature information of a tongue image and analyzes the tongue image to implement objective quantification.

SUMMARY

Embodiments of the present disclosure provide a method, a client, a server and a system for detecting a tongue image and a tongue imager.

According to a first aspect of the present disclosure, the embodiment of the present disclosure provides a method for detecting a tongue image, which is applied to a client for detecting the tongue image, the method comprising:

acquiring the tongue image, recognizing the tongue image by using an image analysis model, and generating and displaying a first label information;

determining, after acquiring a correction information for the first label information, whether to adopt the correction information in accordance with an accuracy corresponding to the correction information, and generating a second label information; and analyzing the tongue image and the second label information by using an assistant diagnosis model, and generating an assistant diagnosis result.

According to a second aspect of the present disclosure, the embodiment of the present disclosure provides a method for detecting a tongue image, which is applied to a server for detecting the tongue image, the method comprising:

acquiring, from a client for detecting the tongue image, the tongue image and a label information; and generating training data in accordance with the tongue image and the label information, and updating an image analysis model and an assistant diagnosis model in accordance with the training data.

According to a third aspect of the present disclosure, the embodiment of the present disclosure provides a client for detecting a tongue image, comprising:

a memory; and a processor, wherein the memory is configured to store computer instructions executable on the processor, the computer instructions, when executed by the processor, causes the processor to perform operations of:

acquiring the tongue image, recognizing the tongue image by using an image analysis model, and generating and displaying a first label information;

determining, after acquiring a correction information for the first label information, whether to adopt the correction information in accordance with an accuracy corresponding to the correction information, and generating a second label information; and analyzing the tongue image and the second label information by using an assistant diagnosis model, and generating an assistant diagnosis result.

According to a fourth aspect of the present disclosure, the embodiment of the present disclosure provides server for detecting a tongue image, comprising:

a memory; and a processor, wherein the memory is configured to store computer instructions executable on the processor, the computer instructions, when executed by the processor, causes the processor to perform operations of:

acquiring, from a client for detecting the tongue image, the tongue image and a label information; and generating training data in accordance with the tongue image and the label information, and updating an image analysis model and an assistant diagnosis model in accordance with the training data.

According to a fifth aspect of the present disclosure, the embodiment of the present disclosure provides a tongue imager, comprising:

a displaying device;

an image capturing device; and the client for detecting a tongue image according to the embodiments as described above, wherein the displaying device and the image capturing device are coupled to the client for detecting the tongue image.

According to a sixth aspect of the present disclosure, the embodiment of the present disclosure provides a system for detecting a tongue image, comprising:

one or more clients for detecting the tongue image, each of which comprises a first device for detecting the tongue image, the first device for detecting the tongue image comprising:

a memory; and a processor, wherein the memory is configured to store computer instructions executable on the processor, the computer instructions, when executed by the processor, causes the processor to perform operations of:

acquiring a tongue image, recognizing the tongue image by using an image analysis model, and generating and displaying a first label information;

determining, after acquiring a correction information for the first label information, whether to adopt the correction information in accordance with an accuracy corresponding to the correction information, and generating a second label information; and analyzing the tongue image and the second label information by using an assistant diagnosis model, and generating an assistant diagnosis result, and a server for detecting the tongue image, which comprises a second device for detecting the tongue image, the second device for detecting the tongue image comprising:

a memory; and a processor, wherein the memory is configured to store computer instructions executable on the processor, the computer instructions, when executed by the processor, causes the processor to perform operations of:

acquiring, from the one or more clients for detecting the tongue image, the tongue image and a label information; and generating training data in accordance with the tongue image and the label information, and updating an image analysis model and an assistant diagnosis model in accordance with the training data.

DETAILED DESCRIPTION

In order to make the objectives, technical solutions, and advantages of the present disclosure clearer and more comprehensible, the embodiments of the present disclosure will be described in detail below with reference to the accompanying drawings. It should be noted that, in the case of no conflicts, the features in the embodiments and the embodiments in the present disclosure may be arbitrarily combined with each other.

Tongue imager in the related arts are generally used independently in hospitals after manufacture, and assistant medical levels thereof are limited to software algorithms which are built into the apparatuses. The tongue imager lacks a product update mechanism after manufacture, which thus goes against promotion and popularization of the tongue imager.

Embodiments of the present disclosure provide a method, a client, a server and a system for detecting a tongue image and a tongue imager. The client for detecting the tongue image acquires the tongue image, recognizes the tongue image by using an image analysis module, and generates and displays a first label information; determines, after acquiring correction information for the first label information, whether to adopt the correction information in accordance with an accuracy corresponding to the correction information, and generates a second label information; and analyzes the tongue image and the second label information by using an assistant diagnosis model, and generates an assistant diagnosis result. By continuously self-learning the correction information of the doctors for the label information, the aforementioned client for detecting the tongue image can continuously improve the accuracy of the system for detecting the tongue image during the use of the system for detecting the tongue image.

Figure 1:
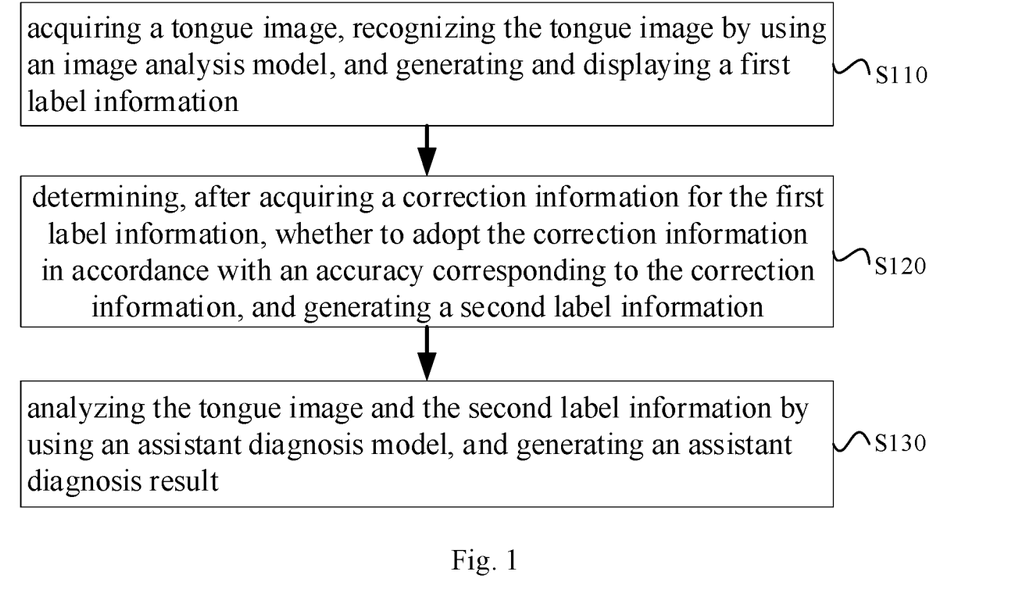
FIG. 1 is a flow chart of a method for detecting a tongue image, which is applied to a client for detecting the tongue image, according to embodiments of the present disclosure.

As shown in FIG. 1, the embodiment of the present disclosure provides a method for detecting a tongue image, which is applied to the client for detecting the tongue image, the method comprising:

Step S110: acquiring the tongue image, recognizing the tongue image by using an image analysis module, and generating and displaying a first label information;

Step S210: determining, after acquiring correction information for the first label information, whether to adopt the correction information in accordance with an accuracy corresponding to the correction information, and generating a second label information;

Step S130: analyzing the tongue image and the second label information by using an assistant diagnosis model, and generating an assistant diagnosis result.

In some embodiments, the method further comprises: acquiring, in accordance with an ID of a doctor who provides the correction information, a historical correction score of the doctor, and determining the accuracy corresponding to the correction information in accordance with the historical correction score of the doctor.

For example, the higher the historical correction score of the doctor, the higher the accuracy corresponding to the correction information provided by the doctor.

In some embodiments, the method further comprises: updating the correction score of the doctor in accordance with a comparison result between the latest correction information of the doctor and the first label information generated by the image analysis model.

For example, updating the correction score of the doctor in accordance with the comparison result between the latest correction information of the doctor and the first label information generated by the image analysis model comprises: increasing the correction score of the doctor if a similarity between the latest correction information of the doctor and the first label information generated by the image analysis model is greater than or equal to a threshold; decreasing the correction score of the doctor if the similarity between the latest correction information of the doctor and the first label information generated by the image analysis model is less than the threshold.

In some embodiments, the first or the second label information includes at least one of a tongue color, a tongue fur, a tongue shape, or presence or absence of a tongue crack.

For example, the tongue color may include any one of a reddish tongue, a whitish tongue, a red tongue, a magenta tongue, a purple tongue, or a cyan tongue.

For example, the tongue shape may include any one of being old and tender, being fat and big, being thin and weak, burr, crack, or tooth mark.

For example, the tongue fur may include any one of a white fur, a yellow fur, a grey fur, a black fur, or a green fur.

In some embodiments, determining whether to adopt the correction information in accordance with the accuracy corresponding to the correction information and the generating the second label information comprises: determining to adopt the correction information and combining the first label information with the correction information for the first label information to generate the second label information if the accuracy corresponding to the correction information is greater than or equal to a confidence threshold; determining not to adopt the correction information and using the first label information as the second label information if the accuracy corresponding to the correction information is less than the confidence threshold.

In some embodiments, the method further comprises: uploading the tongue image and the second label information to a server for detecting the tongue image for updating the image analysis model and the assistant diagnosis model by the server for detecting the tongue image.

In some embodiments, the method further comprises: downloading, from the server for detecting the tongue image, the updated image analysis model and assistant diagnosis model.

For example, the client for detecting the tongue image may periodically download, from the server for detecting the tongue image, the updated image analysis model and assistant diagnosis model.

In some embodiments, the server for detecting the tongue image comprises at least one of a local server or a cloud server. For example, the local server may be a server inside a hospital.

In the embodiments of the present disclosure, the image analysis model and the assistant diagnosis model are implemented by using a software that performs corresponding functions. For example, the image analysis model and the assistant diagnosis model can be run on different computers or different software of the same computer, or the same software integrates functions of the image analysis, the assistant diagnosis, or the like.

The required image analysis function and assistant diagnostic function can be implemented in a variety of ways, such as based on database, based on expert systems, or the like.

For example, the above models can be implemented by machine learning. A first neural network is trained by using the tongue images in the training samples and the corresponding first label information thereof, so that the first neural network can be used as the image analysis model to recognize the input tongue images to generate the first label information. A second neural network is trained by using the tongue images in the samples and the second label information and the corresponding auxiliary diagnostic results thereof, so that the second neural network can be used as the assistant diagnostic model to analyze the input tongue images and the second label information to generate the assistant diagnostic result.

By continuously uploading new data of the samples to the server for detecting the tongue image to train the neural networks, and updating parameters of the neural networks for the client for detecting the tongue image based on the trained models, the accuracy of the client for detecting the tongue image can be further improved.

Figure 2:
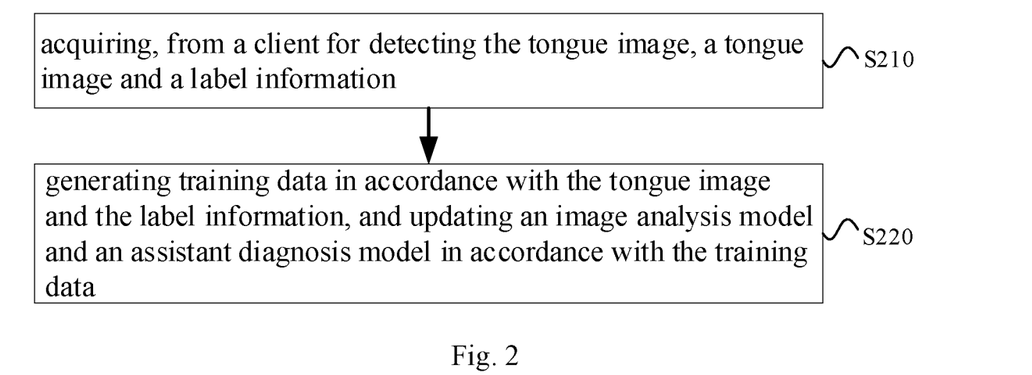
FIG. 2 is a flow chart of a method for detecting the tongue image, which is applied to a server for detecting the tongue image, according to embodiments of the present disclosure.

As shown in FIG. 2, the embodiment of the present disclosure provides a method for detecting a tongue image, which is applied to a server for detecting the tongue image, the method comprising:

Step S210: acquiring, from a client for detecting the tongue image, the tongue image and a label information;

Step S220: generating training data in accordance with the tongue image and the label information, and updating the image analysis model and the assistant diagnosis model in accordance with the training data.

In some embodiments, the server for detecting the tongue image comprises at least one of a local server and a cloud server. For example, the local server may be a server inside a hospital.

In some embodiments, the label information includes at least one of a tongue color, a tongue fur, a tongue shape, or presence or absence of a tongue crack.

For example, the tongue color may include any one of a reddish tongue, a whitish tongue, a red tongue, a magenta tongue, a purple tongue, or a cyan tongue.

For example, the tongue shape may include any one of being old and tender, being fat and big, being thin and weak, burr, crack, or tooth mark.

For example, the tongue fur may include any one of a white fur, a yellow fur, a grey fur, a black fur, or a green fur.

Figure 3:
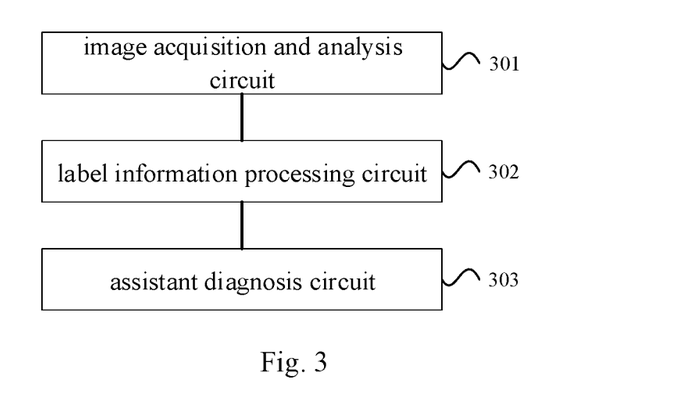
FIG. 3 is a schematic diagram of a device for detecting the tongue image, which is included in the client for detecting the tongue image, according to embodiments of the present disclosure.

As shown in FIG. 3, the embodiment of the present disclosure provides a device for detecting a tongue image, which is included in the client for detecting the tongue image, the device for detecting the tongue image comprising:

an image acquisition and analysis circuit 301 for acquiring the tongue image, recognizing the tongue image by using an image analysis module, and generating and displaying a first label information;

a label information processing circuit 302 for determining, after acquiring a correction information for the first label information, whether to adopt the correction information in accordance with an accuracy corresponding to the correction information, and generating a second label information; and an assistant diagnosis circuit 303 for analyzing the tongue image and the second label information by using an assistant diagnosis model, and generating an assistant diagnosis result.

In some embodiments, the label information processing circuit 302 is further used for acquiring, in accordance with an ID of a doctor who provides the correction information, a historical correction score of the doctor, and determining the accuracy corresponding to the correction information in accordance with the historical correction score of the doctor.

For example, the higher the historical correction score of the doctor, the higher the accuracy corresponding to the correction information provided by the doctor.

In some embodiments, the device for detecting the tongue image further comprises a scoring circuit, the scoring circuit is used for updating the correction score of the doctor in accordance with a comparison result between the latest correction information of the doctor and the first label information generated by the image analysis model.

For example, the scoring module is used for updating the correction score of the doctor in accordance with the comparison result between the latest correction information of the doctor and the first label information generated by the image analysis model in the following way: increasing the correction score of the doctor if a similarity between the latest correction information of the doctor and the first label information generated by the image analysis model is greater than or equal to a threshold; decreasing the correction score of the doctor if the similarity between the latest correction information of the doctor and the first label information generated by the image analysis model is less than the threshold.

In some embodiments, the first and the second label information includes at least one of a tongue color, a tongue fur, a tongue shape, or presence or absence of a tongue crack.

For example, the tongue color may include any one of a reddish tongue, a whitish tongue, a red tongue, a magenta tongue, a purple tongue, or a cyan tongue.

For example, the tongue shape may include any one of being old and tender, being fat and big, being thin and weak, burr, crack, or tooth mark.

For example, the tongue fur may include any one of a white fur, a yellow fur, a grey fur, a black fur, or a green fur.

In some embodiments, the label information processing circuit 302 is used for determining whether to adopt the correction information in accordance with the accuracy corresponding to the correction information and generating the second label information in the following way: determining to adopt the correction information and combining the first label information with the correction information for the first label information to generate the second label information if the accuracy corresponding to the correction information is greater than or equal to a confidence threshold; and determining not to adopt the correction information and using the first label information as the second label information if the accuracy corresponding to the correction information is less than the confidence threshold.

In some embodiments, the device for detecting the tongue image further comprises an information uploading circuit, the information uploading circuit is used for uploading the tongue image and the second label information to the server for detecting the tongue image for updating the image analysis model and the assistant diagnosis model by the server for detecting the tongue image.

In some embodiments, the device for detecting the tongue image further comprises a model downloading and updating circuit, the model downloading and updating circuit is used for downloading, from the server for detecting the tongue image, the updated image analysis model and assistant diagnosis model.

For example, the client for detecting the tongue image may periodically download, from the server for detecting the tongue image, the updated image analysis model and assistant diagnosis model.

In some embodiments, the server for detecting the tongue image comprises at least one of a local server and a cloud server. For example, the local server may be a server inside a hospital.

Figure 4:
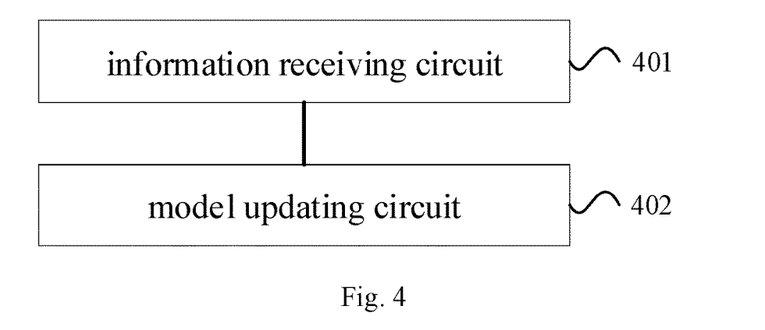
FIG. 4 is a schematic diagram of a device for detecting the tongue image, which is included in the server for detecting the tongue image, according to embodiments of the present disclosure.

As shown in FIG. 4, the embodiment of the present disclosure provides a device for detecting a tongue image, which is included in the server for detecting the tongue image, the device for detecting the tongue image comprising:

an information receiving circuit 401 for acquiring the tongue image and a label information from the client for detecting the tongue image; and a model updating circuit 402 for generating training data in accordance with the tongue image and the label information, and updating the image analysis model and the assistant diagnosis model in accordance with the training data.

In some embodiments, the server for detecting the tongue image comprises at least one of a local server and a cloud server. For example, the local server may be a server inside a hospital.

In some embodiments, the label information includes at least one of a tongue color, a tongue fur, a tongue shape, or presence or absence of a tongue crack.

For example, the tongue color may include any one of a reddish tongue, a whitish tongue, a red tongue, a magenta tongue, a purple tongue, or a cyan tongue.

For example, the tongue shape may include any one of being old and tender, being fat and big, being thin and weak, burr, crack, or tooth mark.

For example, the tongue fur may include any one of a white fur, a yellow fur, a grey fur, a black fur, or a green fur.

In the embodiments of the present disclosure, for the sake of easy understanding and description, the description of the functional circuits corresponding to the functions to be performed is used. It is easy to understand that these functional circuits are functional entities and do not necessarily have to correspond to physically or logically independent entities. These functional entities may be implemented in the form of computer instructions executed by a general-purpose processor running software of the corresponding functions, or may be implemented in one or more hardware modules or integrated circuits in a programmable form, or may be implemented by integrated circuits designed to specifically perform the corresponding functions.

For example, a general-purpose processor may be a central processing unit (CPU), a single chip microcomputer (MCU), a digital signal processor (DSP), or the like.

For example, the programmable integrated circuit may be a field programmable logic circuit (FPGA).

For example, the specific integrated circuit may be an application specific integrated circuit (ASIC).

The embodiment of the present disclosure provides a client for detecting a tongue image, comprising:

a memory;

a processor, wherein the memory is configured to store computer instructions executable on the processor, the computer instructions, when executed by the processor, cause the processor to perform operations of:

acquiring the tongue image, recognizing the tongue image by using an image analysis model, and generating and displaying a first label information;

determining, after acquiring a correction information for the first label information, whether to adopt the correction information in accordance with an accuracy corresponding to the correction information, and generating a second label information; and analyzing the tongue image and the second label information by using an assistant diagnosis model, and generating an assistant diagnosis result.

The embodiment of the present disclosure provides a server for detecting a tongue image, comprising:

a memory;

a processor, wherein the memory is configured to store computer instructions executable on the processor, the computer instructions, when executed by the processor, cause the processor to perform operations of:

acquiring, from a client for detecting the tongue image, the tongue image and a label information; and generating training data in accordance with the tongue image and the label information, and updating an image analysis model and an assistant diagnosis model in accordance with the training data.

In the embodiments of the present disclosure, the memory may be implemented by any type of volatile or non-volatile memory device or a combination thereof, such as a static random access memory (SRAM), an electrically erasable and programmable Read Only Memory (EEPROM), an Erasable Programmable Read Only Memory (EPROM), a Programmable Read Only Memory (PROM), a Read Only Memory (ROM), a Magnetic Memory, a Flash Memory, a Disk or an Optical Disk.

The processor may be logic operation device having data processing capabilities and/or program execution capabilities, such as a central processing unit (CPU) or a field programmable logic array (FPGA) or a single chip microcomputer (MCU) or a digital signal processor (DSP) or an application specific integrated circuit (ASIC) or the like.

The computer instructions include one or more processor operations defined by an instruction set architecture corresponding to a processor, which may be logically included and represented by one or more computer programs.

Figure 5:
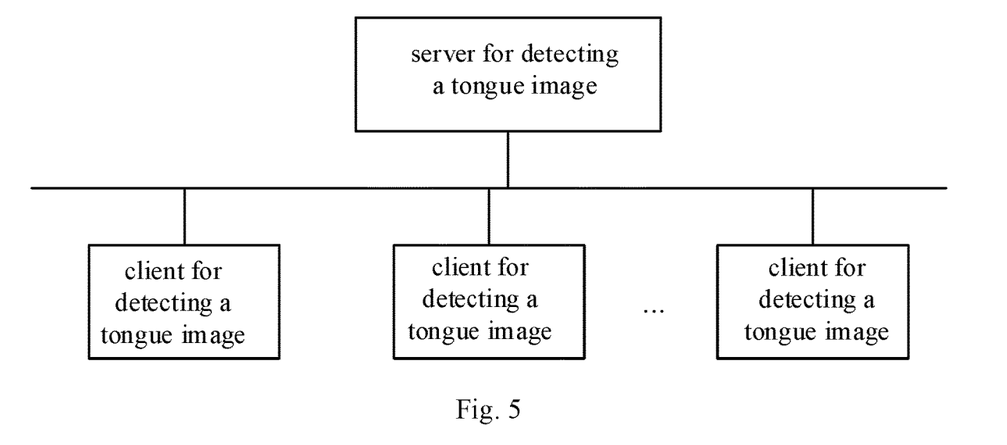
FIG. 5 is a schematic diagram of a system for detecting the tongue image according to embodiments of the present disclosure.

As shown in FIG. 5, the embodiment of the present disclosure provides a server for detecting a tongue image, comprising: one or more clients for detecting a tongue image, and a server for detecting the tongue image. Each of the one or more clients for detecting the tongue image comprises a first device for detecting the tongue image, the first device for detecting the tongue image comprises: an image acquisition and analysis circuit for acquiring the tongue image, recognizing the tongue image by using an image analysis module, and generating and displaying a first label information; a label information processing circuit for determining, after acquiring a correction information for the first label information, whether to adopt the correction information in accordance with an accuracy corresponding to the correction information, and generating a second label information; and an assistant diagnosis circuit for analyzing the tongue image and the second label information by using an assistant diagnosis model, and generating an assistant diagnosis result. The server for detecting the tongue image comprises a second device for detecting the tongue image, the second device for detecting the tongue image comprises: an information receiving circuit for acquiring the tongue image and a label information from the one or more clients for detecting the tongue image; and a model updating circuit for generating training data in accordance with the tongue image and the label information, and updating the image analysis model and the assistant diagnosis model in accordance with the training data.

The embodiment of the present disclosure provides a computer-readable storage medium on which computer instructions are stored, the computer instructions, when executed by the processor, causes the processor to perform operations of:

acquiring the tongue image, recognizing the tongue image by using an image analysis model, and generating and displaying a first label information;

determining, after acquiring a correction information for the first label information, whether to adopt the correction information in accordance with an accuracy corresponding to the correction information, and generating a second label information; and analyzing the tongue image and the second label information by using an assistant diagnosis model, and generating an assistant diagnosis result.

The embodiment of the present disclosure provides a computer-readable storage medium on which computer instructions are stored, the computer instructions, when executed by the processor, cause the processor to perform operations of:

acquiring, from a client for detecting the tongue image, the tongue image and a label information; and generating training data in accordance with the tongue image and the label information, and updating an image analysis model and an assistant diagnosis model in accordance with the training data.

Figure 6:
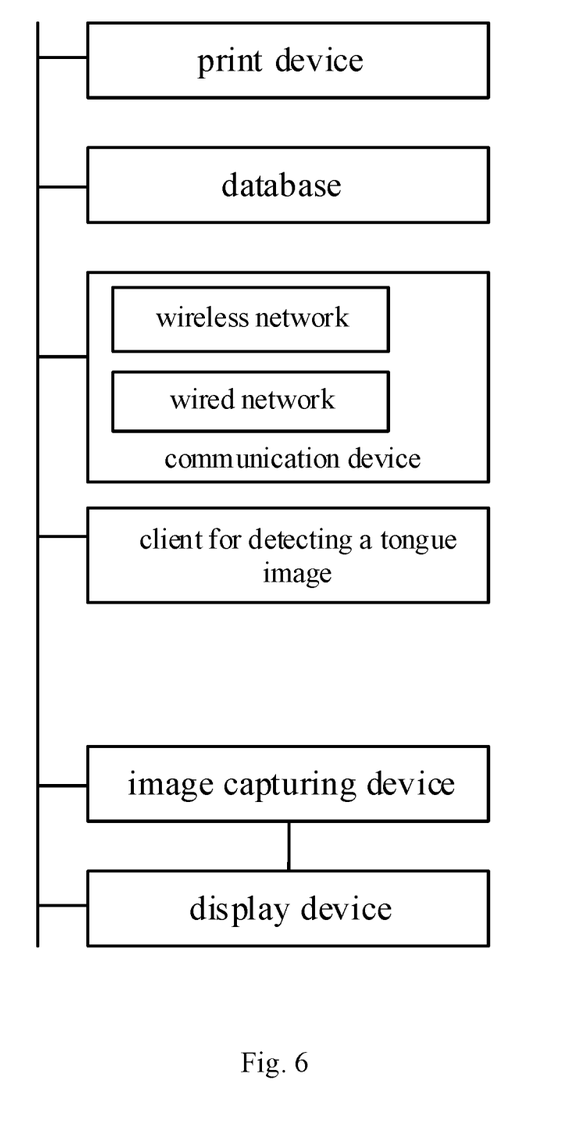
FIG. 6 is a schematic diagram of an exemplary tongue imager according to embodiments of the present disclosure.

As shown in FIG. 6, the present example provides a tongue imager comprising a displaying device, an image capturing device, and a client for detecting a tongue image.

The displaying device is used as a screen displaying system for human-machine interaction. For example, the screen displaying system can play an operational flow and usage precautions of measurement of the tongue imager.

The image capturing device such as imaging device based on imaging element of CCD, CMOS or the like is used as an image capturing system for capturing a tongue image of a patient under certain illumination conditions.

The client for detecting the tongue image executes, on an electronic equipment, an image processing and labeling system for performing image recognition, automatic labeling, and manual correction for the tongue image. Prior to performing the image recognition for the tongue image, a pre-processing may be further performed for the tongue image. The pre-processing includes removing noise or other processing. The image recognition includes recognizing the tongue shape, the tongue fur, the tongue shape, and other tongue features. The manual correction function is used for performing manual correction by a doctor when there is a deviation that occurs between the automatically-recognized tongue feature and the actual tongue image of the patient. The assistant diagnosis system is used for performing disease diagnosis in accordance with the tongue image and the label information.

In some embodiments, the tongue imager further includes a communication device that can be used to implement, for example, a wireless network, a wired network, and/or any combination of a wireless network and a wired network. The network may include a local area network, the Internet, a telecommunications network, an Internet of Things based on the Internet and/or the telecommunications network, and/or any combination of the above networks, and the like. The wired network can communicate by, for example, a twisted pair, a coaxial cable, an optical fiber transmission or the like. For example, the wireless network can adopt a communication method such as a 3G/4G/5G mobile communication network, Bluetooth, Zigbee, Wi-Fi or the like.

The wired network can be used for the transmission of the tongue imager to the PC, and the wireless network is used for connecting the tongue imager to the mobile platform for wireless data transmission. For example, a wired network can be used for the connection of the tongue imager to the apparatus in the hospital. The wireless network can be used for the connection of the tongue imager to the mobile phone of the patient. For example, the patient can obtain the tongue diagnosis result or the like directly through the mobile phone. In some embodiments, the tongue imager is also coupled to a database for storing data such as the tongue image, the label information, the manual correction information of the doctor, the assistant diagnostic result, the label accuracy score of the doctor, or the like.

In some embodiments, the tongue imager is also coupled to a print device such as a laser printer, an inkjet printer or the like, which is used for printing the tongue image and the diagnosis result.

Figure 7:
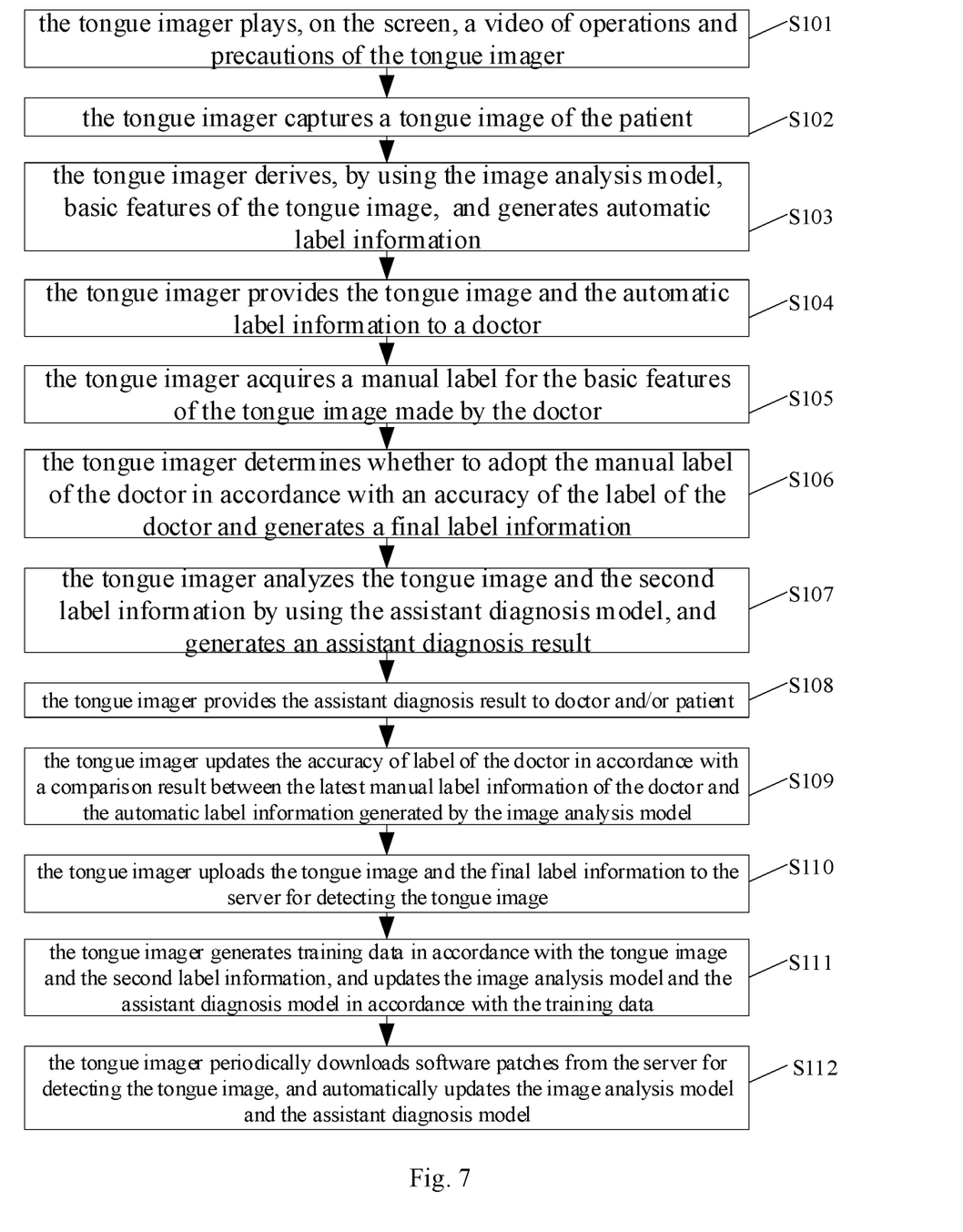
FIG. 7 is a flow chart of an exemplary method for detecting the tongue image according to embodiments of the present disclosure.

As shown in FIG. 7, The present example provides a method for detecting a tongue image, comprising steps of:

Step S101: the tongue imager plays, on the screen, a video of operations and precautions of the tongue imager.

The patient may understand operational details by viewing the video on the screen.

Step S102: the tongue imager captures a tongue image of the patient.

For example, according to operational notes, the patient puts out his or her tongue to a standard position for tongue image capturing. For example, according to requirements of video operations, a size of the captured tongue picture should be ≥6CM*5CM, wherein a ratio of the size of the tongue to an area of the tongue picture should be ≥60%.

Step S103: the tongue imager derives, by using the image analysis model, basic features of the tongue image, such as a tongue color, a tongue shape, a tongue fur, a tongue crack or other features, and generates automatic label information.

For example, the tongue imager performs extraction and analysis of image features by using the image analysis model.

Step S104: the tongue imager provides the tongue image and the automatic label information to an operator (e.g., a doctor) of the tongue imager.

Step S105: the tongue imager acquires a manual label for the basic features of the tongue image (such as the tongue color, the tongue shape, the tongue fur, the tongue crack or other features) made by the operator (e.g., the doctor) of the tongue imager.

Step S106: the tongue imager determines whether to adopt the manual label (i.e., a correction information for a first label information) of the doctor in accordance with an accuracy of the label of the doctor and generates a final label information (i.e., a second label information).

For example, if the doctor makes a first label, the accuracy of his or her label satisfies the requirement by default, his or her manual label information (i.e., the correction information for the first label information) is adopted, the manual label information (i.e., the correction information for the first label information) and the automatic label information (i.e., the first label information) are combined to generate the final label information (i.e., the second label information).

If the doctor does not make the first label, the historical label accuracy of the doctor is acquired in accordance with an ID of the doctor, and it is determined whether to adopt the manual label (i.e., the correction information for the first label information) of the doctor in accordance with the historical label accuracy of the doctor, and the final label information (i.e., the second label information) is generated: if the historical label accuracy of the doctor is greater than or equal to a confidence threshold, it is determined to adopt the manual label information (i.e., the correction information for the first label information) of the doctor, and the automatic label information (i.e., the first label information) and the manual label information (i.e., the correction information for the first label information) are combined to generate the final label information (i.e., the second label information); if the historical label accuracy of the doctor is less than the confidence threshold, it is determined not to adopt the manual label information (i.e., the correction information for the first label information) of the doctor, and the automatic label information (i.e., the first label information) is used as the final label information (i.e., the second label information).

Step S107: the tongue imager analyzes the tongue image and the second label information by using the assistant diagnosis model, and generates an assistant diagnosis result.

Step S108: the tongue imager provides the assistant diagnosis result to the doctor and/or the patient.

Step S109: the tongue imager updates the accuracy of the label of the doctor in accordance with a comparison result between the latest manual label information (i.e., the correction information for the first label information) of the doctor and the automatic label information (i.e., the first label information) generated by the image analysis model.

For example, the accuracy of the label of the doctor is increased if a similarity between the latest manual label information (i.e., the correction information for the first label information) of the doctor and the automatic label information (i.e., the first label information) generated by the image analysis model is greater than or equal to a threshold; the accuracy of the label of the doctor is decreased if the similarity between the latest manual label information (i.e., the correction information for the first label information) of the doctor and the automatic label information (i.e., the first label information) generated by the image analysis model is less than the threshold.

Step S110: the tongue imager uploads the tongue image and the final label information (i.e., the second label information) to the server for detecting the tongue image.

Step S111: the tongue imager generates training data in accordance with the tongue image and the second label information, and updates the image analysis model and the assistant diagnosis model in accordance with the training data.

Step S112: the tongue imager periodically downloads software patches from the server for detecting the tongue image, and automatically updates the image analysis model and the assistant diagnosis model.

Those of ordinary skill in the art will appreciate that all or some of the steps, systems, and device functional blocks/units of the methods disclosed above may be implemented as software, firmware, hardware, and suitable combinations thereof. In a hardware implementation, the division between functional modules/units mentioned in the above description does not necessarily correspond to the division of physical components; for example, one physical component may have multiple functions, or one function or step may be performed by several physical components working together. Certain physical components or all physical components may be implemented as software executed by a processor, such as a central processing unit, digital signal processor or microprocessor, or implemented as hardware, or as an integrated circuit, such as a specific integrated circuit. Such software may be distributed on a computer readable medium, which may include computer storage media (or non-transitory media) and communication media (or transitory media). As is well known to those skilled in the art, the term "computer storage medium" includes volatile and nonvolatile, or removable and non-removable media, implemented in any method or technology for storing information, such as computer readable instructions, data structures, program modules or other data. Computer storage media includes, but is not limited to, RAM, ROM, EEPROM, flash memory or other memory technology, CD-ROM, digital versatile disc (DVD) or other optical disc storage, magnetic cartridge, magnetic tape, magnetic disk storage or other magnetic storage device, or any other medium used to store the desired information that can be accessed by the computer. Moreover, it is well known to those skilled in the art that communication media typically includes computer readable instructions, data structures, program modules or other data in a modulated data signal, such as a carrier wave or other transport mechanism, and can include any information delivery media.

It is to be understood that the disclosure may have other various embodiments. Without departing from the spirit and scope of the disclosure, those skilled in the art may make various corresponding changes and modifications according to the present disclosure, but these corresponding changes and modifications fall into the protection scope of the claims appended to the present disclosure.

What is claimed is:

1. A method for detecting a tongue image, which is applied to a client for detecting the tongue image, the method comprising:
    acquiring the tongue image, recognizing the tongue image by using an image analysis model, and generating and displaying a first label information;
    determining, after acquiring a correction information for the first label information, whether to adopt the correction information in accordance with an accuracy corresponding to the correction information, and generating a second label information; and
    analyzing the tongue image and the second label information by using an assistant diagnosis model, and generating an assistant diagnosis result.

2. The method according to claim 1, the method further comprises:
    acquiring, in accordance with an ID of a doctor who provides the correction information, a historical correction score of the doctor, and determining the accuracy corresponding to the correction information in accordance with the historical correction score of the doctor.

3. The method according to claim 2, the method further comprises:
    updating a correction score of the doctor in accordance with a comparison result between a latest correction information of the doctor and the first label information generated by the image analysis model.

4. The method according to claim 3, wherein:
    updating the correction score of the doctor in accordance with the comparison result between the latest correction information of the doctor and the first label information generated by the image analysis model comprises:
    increasing the correction score of the doctor if a similarity between the latest correction information of the doctor and the first label information generated by the image analysis model is greater than or equal to a threshold; and
    decreasing the correction score of the doctor if the similarity between the latest correction information of the doctor and the first label information generated by the image analysis model is less than the threshold.

5. The method according to claim 1, wherein,
    determining whether to adopt the correction information in accordance with the accuracy corresponding to the correction information and generating the second label information comprises:
    determining to adopt the correction information and combining the first label information with the correction information for the first label information to generate the second label information if the accuracy corresponding to the correction information is greater than or equal to a confidence threshold; and
    determining not to adopt the correction information and using the first label information as the second label information if the accuracy corresponding to the correction information is less than the confidence threshold.

6. The method according to claim 1, the method further comprises:
    uploading the tongue image and the second label information to a tongue image detection server for updating the image analysis model and the assistant diagnosis model by the tongue image detection server.

7. The method according to claim 6, the method further comprises:
    downloading, from the tongue image detection server, the updated image analysis model and the assistant diagnosis model.

8. The method according to claim 1, wherein,
    the first or the second label information includes at least one of a tongue color, a tongue fur, a tongue shape, or presence or absence of a tongue crack.

9. A client for detecting a tongue image, comprising:
    a memory; and
    a processor,
    wherein the memory is configured to store computer instructions executable on the processor, the computer instructions, when executed by the processor, causes the processor to perform the method for detecting the tongue image according to claim 1.

10. A tongue imager, comprising:
    a displaying device;
    an image capturing device; and
    the client for detecting a tongue image according to claim 9,
    wherein the displaying device and the image capturing device are coupled to the client for detecting the tongue image.

11. The tongue imager according to claim 10, further comprising a communication device.

12. A system for detecting a tongue image, comprising:
    one or more clients for detecting the tongue image, each of which comprises a first device for detecting the tongue image, the first device for detecting the tongue image comprising:
    a memory; and
    a processor,
    wherein the memory is configured to store computer instructions executable on the processor, the computer instructions, when executed by the processor, causes the processor to perform operations of:
    acquiring a tongue image, recognizing the tongue image by using an image analysis model, and generating and displaying a first label information;
    determining, after acquiring a correction information for the first label information, whether to adopt the correction information in accordance with an accuracy corresponding to the correction information, and generating a second label information; and
    analyzing the tongue image and the second label information by using an assistant diagnosis model, and generating an assistant diagnosis result, and
    a server for detecting the tongue image, which comprises a second device for detecting the tongue image, the second device for detecting the tongue image comprising:
    a memory; and
    a processor,
    wherein the memory is configured to store computer instructions executable on the processor, the computer instructions, when executed by the processor, causes the processor to perform operations of:
    acquiring, from the one or more clients for detecting the tongue image, the tongue image and a label information; and
    generating training data in accordance with the tongue image and the label information, and updating the image analysis model and the assistant diagnosis model in accordance with the training data.

* * * * *